United States Patent
Wang

(10) Patent No.: US 8,751,259 B2
(45) Date of Patent: Jun. 10, 2014

(54) METHOD, APPARATUS, AND PROGRAM FOR GENERATING DIAGNOSTIC RESULT EXPLANATION REPORTS

(75) Inventor: Caihua Wang, Minato-ku (JP)

(73) Assignee: FUJIFILM Corporation, Tokyo (JP)

( * ) Notice: Subject to any disclaimer, the term of this patent is extended or adjusted under 35 U.S.C. 154(b) by 290 days.

(21) Appl. No.: 13/251,791

(22) Filed: Oct. 3, 2011

(65) Prior Publication Data
US 2012/0084096 A1  Apr. 5, 2012

(30) Foreign Application Priority Data

Oct. 1, 2010 (JP) ................................. 2010-223854
Sep. 26, 2011 (JP) ................................. 2011-209189

(51) Int. Cl.
*G06F 19/00* (2011.01)
*G06F 17/30* (2006.01)
*G06Q 50/22* (2012.01)
*G06Q 50/24* (2012.01)

(52) U.S. Cl.
USPC .................................................. 705/2; 705/3

(58) Field of Classification Search
USPC ............................................................ 705/2
See application file for complete search history.

(56) References Cited

U.S. PATENT DOCUMENTS

| | | | |
|---|---|---|---|
| 2004/0078241 A1* | 4/2004 | Shiobara | 705/3 |
| 2004/0138922 A1 | 7/2004 | Hirose | |
| 2006/0206360 A1* | 9/2006 | Ohta | 705/3 |
| 2010/0231605 A1 | 9/2010 | Moriya et al. | |

FOREIGN PATENT DOCUMENTS

| | | |
|---|---|---|
| JP | 2005217539 A | 8/2005 |
| JP | 2005287632 A | 10/2005 |
| JP | 2006252304 A | 9/2006 |
| JP | 2008-043524 A | 2/2008 |
| JP | 4109084 B2 | 6/2008 |
| JP | 2008250751 A | 10/2008 |
| JP | 2010-024587 A | 2/2010 |

OTHER PUBLICATIONS

Japanese Office Action; Application No. 2011-209189; May 28, 2013.

* cited by examiner

*Primary Examiner* — Hiep V Nguyen
(74) *Attorney, Agent, or Firm* — Sughrue Mion, PLLC

(57) ABSTRACT

A diagnostic result explanation report generating apparatus is equipped with: a diagnostic information storing section, a comment information storing section, a template storing section for storing explanation templates having insertion regions, into which at least portions of the diagnostic information and the comment information are insertable, prepared for each of the various diagnostic results; an input section, for inputting patient specifying information; a diagnostic information obtaining section, for obtaining diagnostic information for a patient, based on the input patient specifying information; a template obtaining section, for obtaining an explanation template which is prepared for a diagnostic result, based on a diagnostic result included in the obtained diagnostic information; a comment information obtaining section, for obtaining comment information from the comment information storing section; and a diagnostic result explanation generating section, for inserting necessary diagnostic information and comment information into the obtained explanation template, to generate a diagnostic result explanation report.

12 Claims, 8 Drawing Sheets

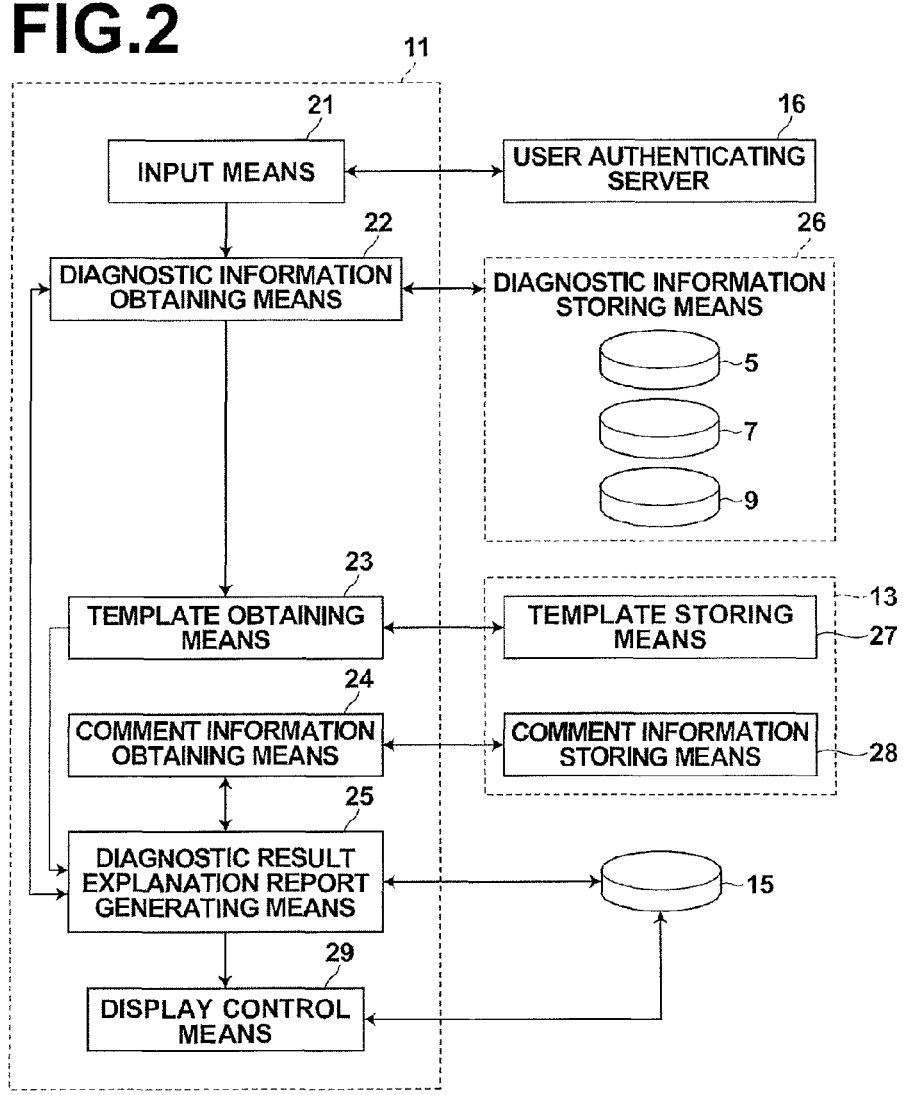

FIG.3

TEST/DIAGNOSTIC RESULT EXPLANATION REPORT FOR PATIENTS — Ta

F1: PATIENT NAME : K11  SEX : K12  DATE OF BIRTH : K13

BASIC INFORMATION  HEIGHT : K14  WEIGHT : K15  BLOOD TYPE : K16

F2: BLOOD TEST RESULTS
- GDP : K21
- ITEM 2 : K22

F3: EXPLANATION OF TEST RESULTS
GDP IS GENERALLY K31 .
K32 IS A NORMAL VALUE.
TESTED VALUE IS K33 , THEREFORE K34
AND K35 MAY BE SUSPECTED.

F4: CT EXAMINATION RESULTS
- MEDICAL OPINION 1 : K41
- K42    K43
- MEDICAL OPINION 2 : K44

F5: EXPLANATION OF TEST RESULTS
- EXPLANATION OF MEDICAL OPINION 1 : K51
- K52    K53
- EXPLANATION OF MEDICAL OPINION 2 : K54

F6: DIAGNOSTIC RESULT
- OFFICIAL NAME OF DISEASE : K61

F7: EXPLANATION OF DIAGNOSTIC RESULT
- EXPLANATION OF DISEASE : K71

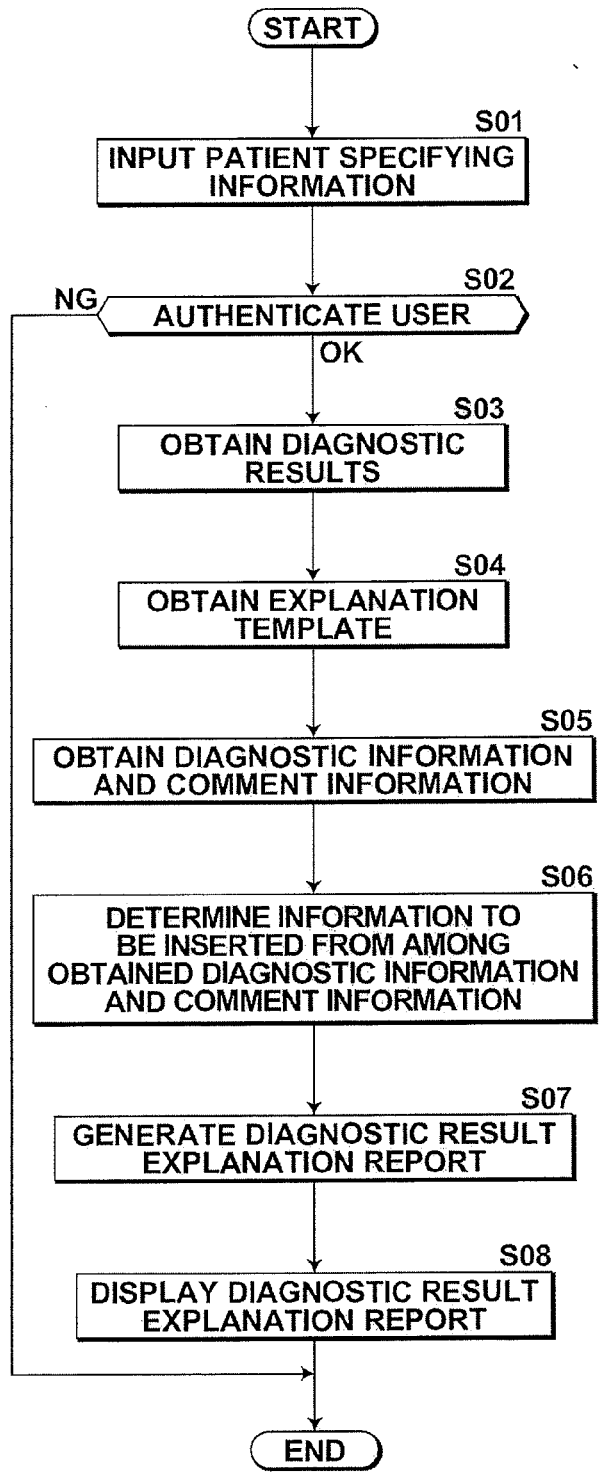
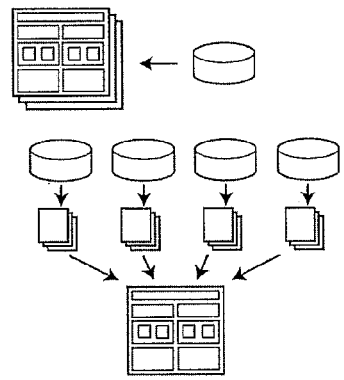
FIG.4

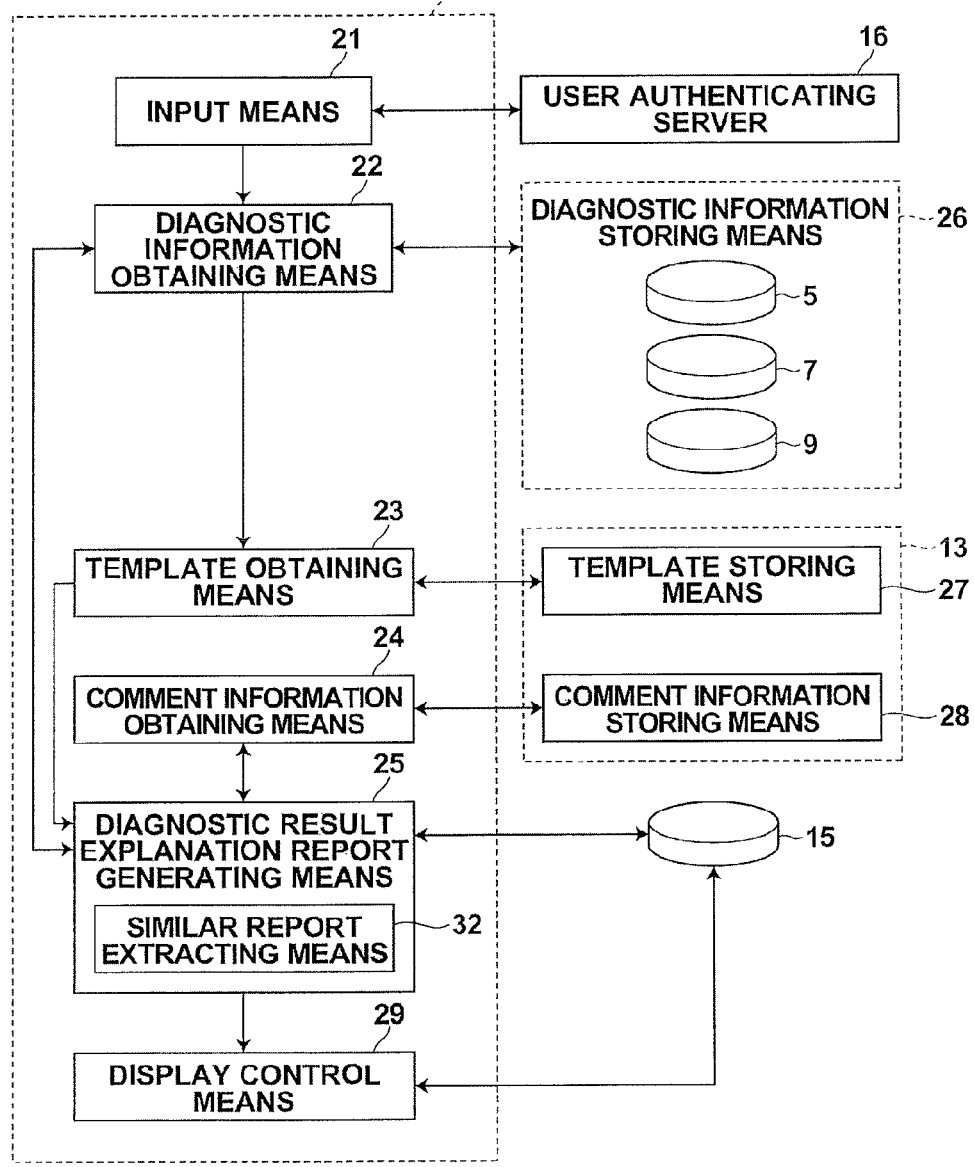

METHOD, APPARATUS, AND PROGRAM FOR GENERATING DIAGNOSTIC RESULT EXPLANATION REPORTS

BACKGROUND OF THE INVENTION

1. Field of the Invention

The present invention is related to a method, an apparatus, and a program for generating diagnostic result explanation reports that explain patients' diagnostic results by adding simple explanations.

2. Description of the Related Art

In the medical field, diagnostic results are explained to patients after necessary examinations are performed. At this time, physicians explain the diagnostic results while referring to diagnostic images, image observation results generated by observing the diagnostic images, and other test results.

There are cases in which patients who lack sufficient basic medical knowledge cannot fully understand the explanations regarding their diagnostic results that include technical jargon and the like. Further, the amounts of time that physicians spend on such explanations are limited. For this reason, techniques for assisting explanations of diagnostic results that ease patient understanding have become focused on.

For example, U.S. Patent Application Publication No. 20040138922 discloses a technique in which reports generated by physicians for medical facilities are referred to and explanatory information for patients are generated. The text, terms, etc. in the explanatory information for patients are changed to simpler or more technical text, terms, etc. according to the comprehension level of patients.

In the technique disclosed in U.S. Patent Application Publication No. 20040138922, the expressions within the reports for medical facilities are changed. However, the contents described in the reports themselves are not changed. Therefore, additional information which is not described within the reports cannot be obtained. For example, there are cases in which contents that physicians are assumed to know as medical professionals, such as general knowledge regarding diseases and differences between symptoms among healthy states and diseased states, are not described in the reports. In such cases, patients cannot sufficiently understand their diagnostic results by referring only to the explanatory information generated based on the reports.

SUMMARY OF THE INVENTION

The present invention has been developed in view of the foregoing circumstances. It is an object of the present invention to provide a method, an apparatus, and a program for generating diagnostic result explanation reports that can improve understanding of diagnostic results by patients.

A diagnostic result explanation report generating apparatus of the present invention is characterized by comprising:

a diagnostic information storing means for storing diagnostic information, which includes patient specifying information that specifies a patient and diagnostic results for the patient;

a comment information storing means for storing comment information regarding various diagnostic results;

a template storing means for storing explanation templates having insertion regions, into which at least a portion of the diagnostic information and the comment information can be inserted, prepared for each of the various diagnostic results;

an input means, for inputting patient specifying information of a patient regarding whom a diagnostic result explanation report is to be generated;

a diagnostic information obtaining means, for obtaining diagnostic information for a patient from the diagnostic information storing means, based on the input patient specifying information;

a template obtaining means, for obtaining an explanation template which is prepared for a diagnostic result, based on a diagnostic result included in the obtained diagnostic information;

a comment information obtaining means, for obtaining comment information from the comment information storing means; and a diagnostic result explanation generating means, for inserting necessary diagnostic information and comment information obtained from the diagnostic information storing means and the comment information storing means into the obtained explanation template, to generate a diagnostic result explanation report.

A diagnostic result explanation report generating method of the present invention is characterized by comprising the steps of:

storing diagnostic information, which includes patient specifying information that specifies a patient and diagnostic results for the patient;

storing comment information regarding various diagnostic results;

storing explanation templates having insertion regions, into which at least a portion of the diagnostic information and the comment information can be inserted, prepared for each of the various diagnostic results;

inputting patient specifying information of a patient regarding whom a diagnostic result explanation report is to be generated;

obtaining diagnostic information for a patient from among the stored diagnostic information, based on the input patient specifying information;

obtaining an explanation template which is prepared for a diagnostic result, based on a diagnostic result included in the obtained diagnostic information;

obtaining comment information from among the stored comment information; and inserting necessary diagnostic information and comment information from among the obtained diagnostic information and stored comment information into the obtained explanation template, to generate a diagnostic result explanation report.

A diagnostic result explanation report generating program of the present invention is characterized by causing a computer to function as:

a diagnostic information storing means for storing diagnostic information, which includes patient specifying information that specifies a patient and diagnostic results for the patient;

a comment information storing means for storing comment information regarding various diagnostic results;

a template storing means for storing explanation templates having insertion regions, into which at least a portion of the diagnostic information and the comment information can be inserted, prepared for each of the various diagnostic results;

an input means, for inputting patient specifying information of a patient regarding whom a diagnostic result explanation report is to be generated;

a diagnostic information obtaining means, for obtaining diagnostic information for a patient from the diagnostic information storing means, based on the input patient specifying information;

a template obtaining means, for obtaining an explanation template which is prepared for a diagnostic result, based on a diagnostic result included in the obtained diagnostic information;

a comment information obtaining means, for obtaining comment information from the comment information storing means; and a diagnostic result explanation generating means, for inserting necessary diagnostic information and comment information obtained from the diagnostic information storing means and the comment information storing means into the obtained explanation template, to generate a diagnostic result explanation report.

In the present invention, the diagnostic results include various diagnostic results obtained at a medical facility. Examples of such diagnostic results include: the name of a disease; diagnostic images obtained for image diagnosis; and test results, such as blood test results and biopsy results.

The comment information is information that explains the names of disease, and diagnostic standards of image diagnosis and test results. For example, the comment information may include: text that explains the names of diseases, the symptoms of diseases, treatment methods for diseases, and the efficacies of treatment methods in simple words; statistical data that represent the numerical ranges of model test results; human anatomical charts; the names of anatomical structures included in the anatomical charts and explanations of the functions thereof; and images, such as standard images obtained by imaging a model standard human. The comment information may also include audio messages.

The diagnostic information includes at least patient specifying information, such as patient ID's and the names of patients. In addition, the diagnostic information includes at least one piece of information related to patient diagnoses. Examples of pieces of information related to patient diagnoses include: various test results; electronic charts; diagnostic images obtained by imaging with various modalities; image observation reports; and examination histories.

The diagnostic result explanation report generating apparatus may adopt a configuration, wherein:

the template storing means stores a plurality of explanation templates having different levels of detail for each of the various diagnostic results.

The diagnostic result explanation report generating apparatus may adopt a configuration, wherein:

the input means also inputs the level of detail of explanations; and the template obtaining means obtains an explanation template corresponding to the input level of detail.

The diagnostic result explanation report generating apparatus may adopt a configuration, wherein:

the diagnostic result explanation report generating means inserts a diagnostic image from among the diagnostic information of the patient into an insertion region of the template. In this case, the diagnostic result explanation report generating means may insert an anatomical chart corresponding to the diagnostic image of the patient from among the diagnostic information into an insertion region of the template.

The diagnostic result explanation report generating apparatus may adopt a configuration, wherein:

the diagnostic result explanation report generating means inserts a model image that represents the same portion as that represented by the diagnostic image of the patient from among the diagnostic information into an insertion region of the template.

The diagnostic result explanation report generating apparatus may adopt a configuration, wherein:

the input means inputs the patient specifying information via the Internet.

The diagnostic result explanation report generating apparatus may further comprise:

a diagnostic result explanation storing means, for storing the diagnostic result explanation reports generated by the diagnostic result explanation report generating means; and an editing means, for editing the stored diagnostic result explanation reports.

According to the apparatus, the method, and the program for generating diagnostic result explanation reports of the present invention, the explanation templates having insertion regions, into which at least a portion of the diagnostic information and the comment information can be inserted, are prepared and stored for each of the various diagnostic results. Patient specifying information of a patient regarding whom a diagnostic result explanation report is to be generated is input, and diagnostic information for a patient is obtained from among the stored diagnostic information, based on the input patient specifying information. Next, an explanation template, which is prepared for a diagnostic result, is obtained, based on a diagnostic result included in the obtained diagnostic information. Finally, the diagnostic result explanation report is generated by inserting necessary diagnostic information and comment information from among the obtained diagnostic information and stored comment information into the obtained explanation template. Therefore, diagnostic result explanation reports, in which diagnostic information of patients and comment information related to the diagnostic information of patients are inserted, can be generated. As a result, user comprehension of diagnostic results can be improved.

The diagnostic result explanation report generating apparatus may adopt a configuration, wherein: the template storing means stores a plurality of explanation templates having different levels of detail for each of the various diagnostic results. In this case, diagnosis result explanation reports having different levels of detail can be generated. Therefore, diagnosis result explanation reports corresponding to user comprehension levels can be generated, and as a result, the comprehension of diagnostic results can be improved.

The diagnostic result explanation report generating apparatus may adopt a configuration, wherein: the input means also inputs the level of detail of explanations; and the template obtaining means obtains an explanation template corresponding to the input level of detail. In this case, diagnosis result explanation reports having levels of detail corresponding to the input level of detail can be generated, and the comprehension of diagnostic results can be improved.

The diagnostic result explanation report generating apparatus may adopt a configuration, wherein: the diagnostic result explanation report generating means inserts a diagnostic image from among the diagnostic information of the patient into an insertion region of the template. In this case, diagnosis result explanation reports that include diagnostic images of patients can be generated, and the comprehension of diagnostic results can be improved.

Further, in the case described above, the diagnostic result explanation report generating means may insert an anatomical chart corresponding to the diagnostic image of the patient from among the diagnostic information into an insertion region of the template. If this configuration is adopted, the diagnostic image can be better understood by referring to the anatomical chart in the completed diagnostic result explanation report, thereby improving the comprehension of diagnostic results. Similarly, the diagnostic result explanation report generating means may insert a model image that represents the same portion as that represented by the diagnostic image of the patient from among the diagnostic information into an insertion region of the template. If this configuration is adopted, the diagnostic image can be better understood by referring to the model image in the completed diagnostic result explanation report, thereby improving the comprehension of diagnostic results.

The diagnostic result explanation report generating apparatus may adopt a configuration, wherein: the input means inputs the patient specifying information via the Internet. In this case, the locations at which the diagnostic result explanation reports can be generated will be less limited.

The diagnostic result explanation report generating apparatus may further comprise: the diagnostic result explanation storing means, for storing the diagnostic result explanation reports generated by the diagnostic result explanation report generating means; and the editing means, for editing the stored diagnostic result explanation reports. In this case, the diagnostic result explanation reports may be edited as necessary, and the generated or edited diagnostic result explanation reports can be stored. Therefore, the generated or edited diagnostic result explanation reports can be more actively utilized.

BRIEF DESCRIPTION OF THE DRAWINGS

FIG. 2 is a functional block diagram of the diagnostic result explanation report generating apparatus according to the first embodiment of the present invention.

FIG. 3 is a diagram that illustrates an example of an explanation template.

FIG. 4 is a flow chart that illustrates the processes performed by the diagnostic result explanation report generating apparatus according to the first embodiment of the present invention.

FIG. 8 is a functional block diagram of the diagnostic result explanation report generating apparatus according to a third embodiment of the present invention.

DESCRIPTION OF THE PREFERRED EMBODIMENTS

Hereinafter, embodiments of the diagnostic result explanation report generating apparatus, the diagnostic result explanation report generating method, and the diagnostic result explanation report generating program of the present invention will be described in detail with reference to the attached drawings.

Figure 1:
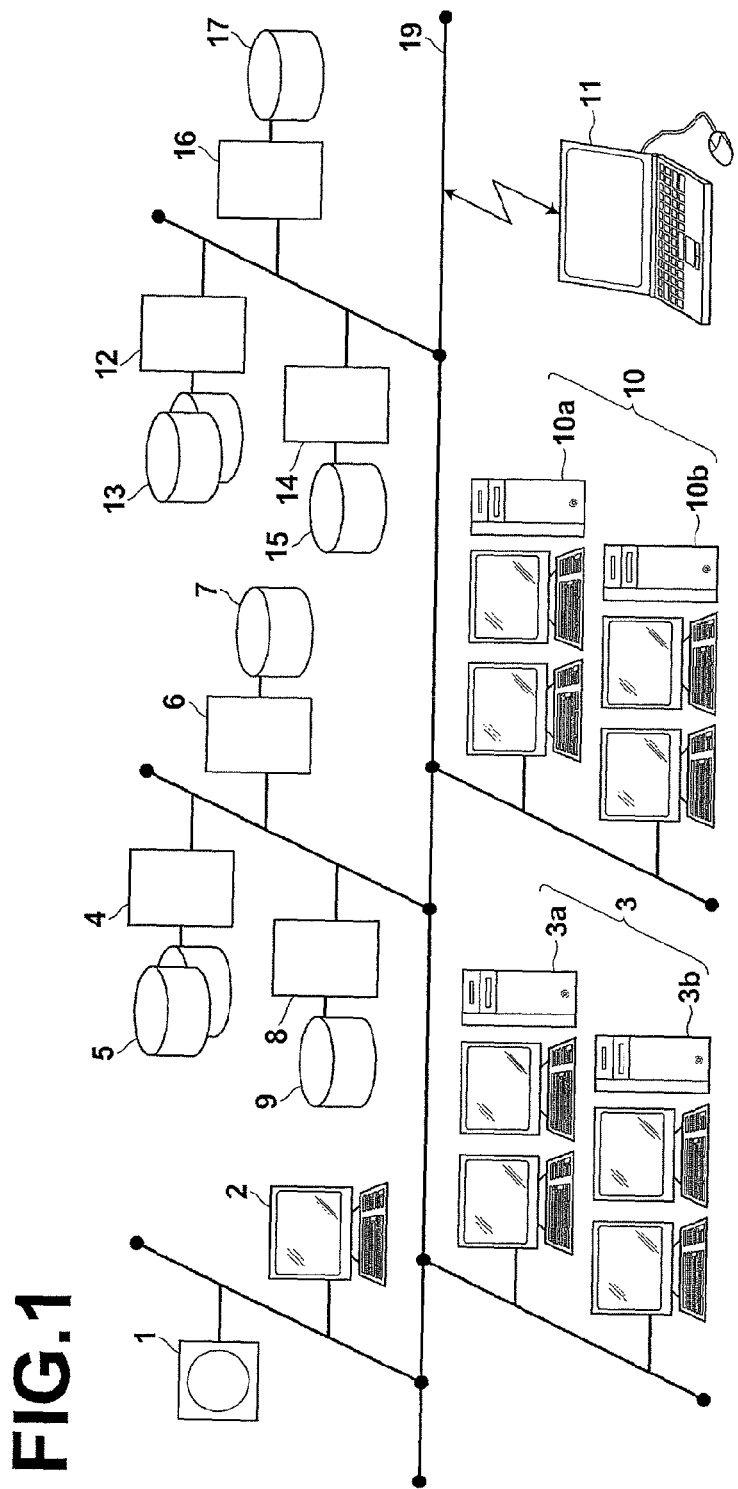
FIG. 1 is a diagram that illustrates the hardware configuration of a diagnostic result explanation report generating apparatus according to a first embodiment of the present invention.

FIG. 1 is a diagram that illustrates the schematic structure of a medical information system in which a diagnostic result explanation report generating apparatus according to an embodiment of the present invention is incorporated. As illustrated in FIG. 1, the system is equipped with: an imaging modality 1 for obtaining medical images; an image quality assurance checking work station (QA-WS) 2; image diagnosis medical work stations 3 (3a, 3b); an image information managing server 4; an image information database 5; an image observation report managing server 6; an image observation report database 7; an electronic chart managing server 8; an electronic chart database 9; diagnostic medical work stations 10 (10a, 10b); a patient terminal 11; a comment information managing server 12; a comment information database 13; a diagnostic result explanation report managing server 14; a diagnostic result explanation report database 15; a user authenticating server 16; and a user managing database 17. Each component is connected to each other so as to be capable of communications via a network 19. The components except for the databases are controlled by programs installed from recording media, such as CD-ROM's. The programs may alternatively be downloaded via a network, such as the Internet, from a server, and then installed.

The imaging modality 1 includes an apparatus that generates three dimensional image data that represent three dimensional images of examination target portions of subjects by imaging these portions, attaches data defined by DICOM standards to the image data, and outputs the image data. Specific examples of the imaging apparatus 1 include: a CT (Computed Tomography) apparatus; an MR (Magnetic Resonance) apparatus; an X ray imaging apparatus; a PET (Positron Emission Tomography) apparatus, and an ultrasound imaging apparatus. Note that hereinafter, combinations of the image data that represent subjects and the data attached to the image data will be referred to as "image information". That is, the "image information" includes text data related to images.

The QA-WS 2 is constituted by a general use processing apparatus (computer), one or two high resolution displays, and input devices such as a keyboard and a mouse. Software that assists the work of examining technicians is incorporated into the processing apparatus. The QA-WS 2 receives image information according to the DICOM standard from the modality 1 by functions realized by executing the software program. Then, the image data included in the received image information and the contents of the attached data are displayed on a screen, to solicit the examination technician for confirmation. Image information which has been confirmed by the examination technician is transferred to the image information managing server 4 via the network 19, and a request to register the image information in the image information database 5 is sent.

The image diagnosis medical work station 3 is utilized by radiologists to observe images and to generate image observation reports. The image diagnosis medical work station 3 is constituted by a processing apparatus, one or two high resolution displays, and input devices such as a keyboard and a mouse. This apparatus sends requests to view images to the image information managing server 4, displays images received from the image information managing server 4, assists in automatic detection and emphasized display of portions of images that may be diseased, assists generation of image observation reports, sends requests to register and view image observation reports to the image observation report managing server 6, and displays image observation reports received from the image observation report managing server 6.

The image information managing server 4 is a comparatively high performance general use computer which has built in software that provides the functions of a DBMS (DataBase Management System). The image information managing server 4 is equipped with a high capacity storage that constitutes the image information database 5. In the present specification, the storage that constitutes each database may be a high capacity hard disk device connected to the managing server corresponding thereto by a data bus. Alternatively, the storage may be an NAS (Network Attached Storage) or an SAN (Storage Area Network) which is connected to the network 19.

The image information database 5 has image data that represent images of subjects and additional data attached thereto registered therein. The attached additional data may include: image ID's for identifying individual images; patient ID's for identifying subjects; examination ID's for identifying examinations; unique ID's (UID's) which are assigned to each piece of image information; the time/date of examination when the image information was generated; the type of modality utilized during examinations to obtain image information; patient information such as the name, age, and sex of the patient; examined portions (imaged portions); imaging conditions (whether an imaging agent was utilized/utilized pigment, radiation nuclide, radiation dosage, etc.); and series numbers or collection numbers in the case that a plurality of images are obtained during a single examination. The image data are managed as XML or SGML data files.

When the image information managing server 4 receives requests to register image information from the QA-WS 2, the image information is organized into a format for the database and registered in the image information database 5.

In addition, when viewing requests are received from the image diagnosis medical work stations 3, the image information managing server 4 searches for the image information from among image information registered in the image information database 5, and transmits extracted image information to the image diagnosis medical work station 3 that sent the request.

When a user such as a radiologist performs operations to request viewing of an image for observation, the image diagnosis medical work station 3 transmits a viewing request to the image information managing server 4, and obtains the image information necessary for observation. Then, the image diagnosis medical work station 3 displays the image information on the screen of a monitor, and executes automatic disease detection processes and the like according to requests input by the radiologist.

Further, the image diagnosis medical work station 3 displays a report generating screen that assists generation of image observation reports on the monitor. When the radiologist inputs text that represents the contents of diagnosis (medical opinions, etc.) performed based on image observation, the image diagnosis medical work station 3 generates an image observation report, in which the input information and the image which was the target of observation (hereinafter, observation target image) is recorded. In the case that there are a plurality of observation target images, a representative image that had the greatest influence on the diagnosis is recorded in the image observation report. The image diagnosis medical work station 3 transfers the generated image observation report to the image observation report managing server 6 via the network 19, and sends a request to register the image observation report in the image observation report database 7.

The image observation report managing server 6 is a comparatively high performance general use computer which has built in software that provides the functions of a DBMS (DataBase Management System). When the image observation report managing server 6 receives requests to register image observation reports from the image diagnosis medical work stations 3, the image observation reports are organized into a format for the database and registered in the image observation report database 7.

The image observation report database 7 has registered therein image ID's for identifying observation target images or representative images, observer ID's for identifying radiologists who performed image observation, positional information related to regions of interest, medical opinions, and the degrees of certainty of the medical opinions, for example. In addition, examination ID's and patient ID's, obtained by referring to the additional data attached to the image information, and further, image data that represent the observation target images or the representative images themselves may also be registered in the image observation report database 7. The image data may be copies of the image data which are registered in the image information database 5. Alternatively, the image data may be reduced image data, which have fewer numbers of pixels (thinned out) than the image data registered in the image information database 5. As a further alternative, the image data may be link data that indicate the storage locations of the image data within the image information database 5 and the file names thereof. In addition, the positional information related to regions of interest may be registered in the image information database 5 as part of the additional data attached to the image data, instead of in the image observation report database 7. Note that the image observation reports are managed as XML or SGML data files.

When viewing requests are received from the image diagnosis medical work stations 3, the image observation report managing server 6 searches for the image observation reports from among image observation reports registered in the image observation report database 7, and transmits extracted image observation reports to the image diagnosis medical work station 3 that sent the request.

The electronic chart managing server 8 is a comparatively high performance general use computer which has built in software that provides the functions of a DBMS (DataBase Management System). The electronic chart managing server 8 is equipped with a high capacity storage that constitutes the electronic chart database 9. When a request to update chart data is received, the electronic chart managing server 8 searches the electronic chart database 9 for the chart data, reads the chart data into a memory, updates the contents thereof in the memory, then writes the updated chart data into the storage. The contents of the electronic chart database 9 are updated in this manner.

Note that the electronic chart data registered in the electronic chart database 9 are managed as XML or SGML data files. The electronic chart data includes: patient information which is registered during a first examination; history of visits by the patient; history of examinations; history of treatment such as medications; and information necessary to perform diagnosis and treatment, such as previous diseases, preexisting conditions, and allergies. Further, reduced image data or link data related to image data may be recorded as an item within the history of examinations in the same manner as in the image observation reports.

The diagnostic medical work stations 10 are apparatuses which are utilized by diagnosing physicians to refer to image observation reports and images which were the targets of observation. Each diagnostic medical work station 10 is constituted by a processing apparatus, one or two high resolution displays, and input devices, such as a keyboard and a mouse. A chart data generating function for recording the history of examinations, tests, and treatments (such as medications) for each patient as electronic data, and a test ordering function for generating and transmitting order data for tests to an ordering system (not shown) of a radiology department, are built in to the processing apparatus.

The diagnostic medical work station 10 generates a new piece of chart data, in which patient information and the purpose of examination are recorded, upon an initial visit by a patient. The diagnostic medical work station 10 transfers the generated piece of chart data to the electronic chart managing server 8 via the network 19, and sends a request to register the piece of chart data in the electronic chart database 9. When the request to register the piece of chart data is received, the electronic chart managing server 8 organizes the piece of chart data into a format for the database, and registers the piece of chart data in the electronic chart database 9.

In the case that tests are ordered by the test ordering function during the course of examination, the diagnostic medical work station 10 adds a test number, a test date, etc., which are issued by a system at the radiology department, to the chart data. Further, after the tests are completed, radiologists have generated image observation reports, and a diagnosing physician refers to the image observation reports, a portion of the information recorded in the image observation report (the medical opinions of the radiologists, for example) is added to the chart data.

Information input by the diagnosing physician themselves is also added to the chart data as necessary. For example, with respect to tests that do not accompanying imaging, such as blood tests, medical opinion information input by the diagnosing physician who refers to the test results are also added to the chart data. In addition, information regarding records of treatment, such as prescribed medications, is also input by the diagnosing physician and added to the chart data. The diagnostic medical work station 10 transfers updated chart data or difference data that indicates only changed portions to the electronic chart managing server 8, and sends a request to update the corresponding chart data.

The electronic chart database 9 is constituted by: a patient information table; a patient test history table; a patient examination history table; a test information table; and an examination information table. The patient information table is newly registered with patient attributes upon a first visit by a patient. Specifically, a patient ID for identifying the patient, the date of birth of the patient, the sex of the patient, etc. are correlated in the patient information table. The patient test history table is registered when a test is scheduled or executed for the patient. The patient ID of the patient and the test ID's that identify tests that the patient underwent are correlated in the patient test history table to manage the history of tests administered on the patient. The patient examination history table is registered when an examination is scheduled for the patient or when the patient is actually examined. The patient ID of the patient and examination ID's that the patients underwent are correlated to manage the history of examinations that the patient undergoes. The test information table registers the contents of various tests. Specifically, test ID's test dates, test types (CT imaging, blood tests, etc.), tested portions (chest, abdomen, etc.) a representative image ID that identifies a representative image from among obtained images, etc. are correlated in the test information table. New information is registered when a test is scheduled, for example. However, the representative image ID is set after image diagnosis is performed or when a diagnosis is confirmed by an examination. The examination information table registers the contents of various examinations. Specifically, examination ID's examination dates, confirmed diagnosis information regarding the contents of diagnoses confirmed during examinations, etc. are correlated in the examination information table.

The patient terminal 11 is a notebook computer utilized by patients when referring to diagnostic results, and is constituted by a processing apparatus, a display, and input devices such as a keyboard and a mouse. This apparatus sends and receives images to and from the image information managing server 4, sends and receives image observation report information to and from the image observation report managing server 6, sends and receives comment information to and from the comment information managing server 12, sends and receives diagnostic result explanation reports to and from the diagnostic result explanation report managing server 14, and generates, registers, displays, and edits diagnostic result explanation reports that utilize each of the sent and received pieces of information. The patient terminal 11 is connected to the network 19 via the Internet.

The diagnostic result explanation report generating apparatus according to the embodiment of the present invention is realized as a client server type system, in which the patient terminal 11, the image information managing server equipped with the image information database 5, the image observation report managing server 6 equipped with the image observation report database 7, the comment information managing server 12 equipped with the comment information managing database 13, the comment information managing server 12 equipped with the comment information managing database 13, the diagnostic result explanation report managing server 14 equipped with the diagnostic result explanation report database 15, and the user authenticating server 16 are connected via the network 19. The details of the system will be described later.

The patient terminal newly generates diagnostic result explanation reports according to requests input by patients, transfers the diagnostic result explanation reports to the diagnostic result explanation report managing server 14 via the network, and sends requests to register the diagnostic result explanation report information in the diagnostic result explanation report database 15. When a request to register diagnostic result explanation report information is received, the diagnostic result explanation report managing server 14 organizes the diagnostic result explanation report information into a format for the database, and sends the organized diagnostic result explanation report information to the diagnostic result explanation report database 15. The details of the diagnostic result explanation report will be described later.

Meanwhile, pieces of information input by patients themselves are also added to the diagnostic result explanation reports as necessary. The patient terminal 11 transfers diagnostic result explanation report data or difference data that indicates only changed portions to the diagnostic result explanation report managing server 14, and sends a request to update the corresponding diagnostic result explanation report data.

The comment information managing server 12 is a comparatively high performance general use computer which has built in software that provides the functions of a DBMS (DataBase Management System). The comment information managing server 12 is equipped with a high capacity storage that constitutes the comment information database 13. When a request to search for a piece of comment information is received, the comment information managing server 12 searches the comment information database 13 for the piece of comment information, and reads the piece of comment information into a memory. In addition, the comment information managing server 12 receives requests to register and update comment information. In the case that a request to update comment information is received, the contents of the comment information are updated in the memory, then written into the memory. The contents of the comment information database 13 are updated in this manner. In addition, the comment information database 13 has registered therein pieces of information that explains diagnostic results for a plurality of different types of diagnostic results as comment information. For example, alternate names or abbreviated names of diseases, principal symptoms, treatment methods, and efficacies of the treatment methods are stored for each disease name. In addition, interpretation methods for test results, how diseases influence test results, and suspected diseases corresponding to test results are stored for each of a variety of test results. Further, electronic medical text data that explain the states of healthy organs, include anatomical charts, and describe the functions and names of various organs, as well as images of standard human models are also stored in the comment information database 13.

The diagnostic result explanation report managing server 14 is a comparatively high performance general use computer which has built in software that provides the functions of a DBMS (DataBase Management System). The diagnostic result explanation report managing server 14 is equipped with a high capacity storage that constitutes the diagnostic result explanation report database 15. When a request to update diagnostic result explanation report data is received, the diagnostic result explanation report managing server 14 searches the diagnostic result explanation report database 15 for the diagnostic result explanation report data, reads the diagnostic result explanation report data into a memory, updates the contents thereof in the memory, then writes the updated diagnostic result explanation report data into the storage. The contents of the diagnostic result explanation report database 15 are updated in this manner.

The user authenticating server 16 has software for managing user ID's passwords, and access rights of users installed therein. The patient ID's and patient passwords can be registered, changed, or deleted from medical facility staff terminals connected to the network by hospital employees. The user authenticating server 16 receives requests for registration and changes, and registers, updates, and deletes patient ID's correlated with patient passwords in the user managing database 17.

In addition, the user authenticating server 16 receives authentication requests from the patient terminal 11, judges whether user ID's and passwords match, and transmits the results of judgment to the patient terminal 11. Note that access right data are transmitted along with the results of judgment in cases that the user ID's and passwords match.

The image ID's the test ID's the patient ID's and examination ID's within each of the databases are of the same format, and these ID's are employed to correlate the databases and tables. For example, test ID's of tests that a patient has undergone in the past are obtained from the patient test history table based on a patient ID in the patient information table. Then, an image ID of a representative image obtained by chest CT imaging (for different types of tests/imaged portions) performed in the past for the patient can be obtained based on the test ID. Further, image data that represent the representative image can be obtained from the image information database 5 based on the representative image ID, or medical opinions input with respect to the representative image can be obtained from the image observation report database 7.

The network 19 is a local area network that connects various apparatuses within a hospital. However, in the case that the image diagnosis medical work stations 3 are provided at a different hospital or clinic, the network 19 may be local area networks of hospitals which are connected to each other via the Internet or via dedicated lines. In both cases, it is desirable for the network 19 to be that which enables high speed transfer of image information, such as an optical network.

Hereinafter, the details of the diagnostic result explanation report generating apparatus according the first embodiment of the present invention will be described.

FIG. 2 is a block diagram that schematically illustrates the configuration of the diagnostic result explanation report generating apparatus according to the first embodiment of the present invention. As illustrated in FIG. 2, the apparatus is constituted by: a diagnostic information storing means 26; a comment information storing means 28; a template storing means 27 for storing a plurality of templates which are prepared for various diagnostic results; an input means 21; a diagnostic information obtaining means 22; a template obtaining means 23; a comment information obtaining means 24; a diagnostic result explanation report generating means 25; the user authenticating server 16 that performs user authentication according to input via the input means 21; a display control means 29; and the diagnostic result explanation report database 15. The patient terminal 11 functions as the input means 21, the diagnostic information obtaining means 22, the template obtaining means 23, the comment information obtaining means 24, the diagnostic result explanation report generating means 25, and the display control means 29, by necessary portions of a diagnostic result explanation report generating program being loaded into a memory thereof.

The diagnostic information obtaining means 22 obtains patient specifying information that specifies patients and diagnostic information that includes diagnostic results of patients. The diagnostic information obtaining means 22 is constituted by the image information database 5, the image observation report database 7, and the electronic chart database 9. Note that the diagnostic information includes at least patient specifying information, such as a patient ID and the name of the patient, and one or more pieces of information related to the diagnosis of the patient. The pieces of information related to the diagnosis of the patient may be any information that relates to the diagnosis of the patient. Examples of such pieces of information include: various test results, electronic charts, diagnostic images obtained by various modalities; image observation reports; and test histories. In addition, in the present invention, the diagnostic results may include various results of diagnosis provided by medical facilities. Examples of such diagnostic results include: the names of diseases; diagnostic images for image diagnosis; and various test results, such as the results of blood tests and the results of biopsies.

In addition, the present invention is not limited to the first embodiment. The databases that constitute the diagnosis information storing means 26 may be constituted by various system formats which are employed at each of a plurality of hospitals. In addition, an apparatus that stores other diagnostic information, such as a biopsy information server that stores the test results of a biological tissue testing department, may also be connected to the diagnostic information storing means 26 via the network 19.

The comment information storing means 28 stores comment information regarding various diagnostic results, and is constituted by the comment information database 13.

The comment information is information that explains the names of disease, and diagnostic standards of image diagnosis and test results. For example, the comment information may include: text that explains the names of diseases, the symptoms of diseases, treatment methods for diseases, and the efficacies of treatment methods in simple words; statistical data that represent the numerical ranges of model test results; human anatomical charts; the names of anatomical structures included in the anatomical charts and explanations of the functions thereof; and images, such as model images obtained by imaging a model standard human. The comment information may also include audio messages.

The comment information database 13 stores electronic medical texts and samples of past clinical data. A normal range of test results, images of healthy tissue, and anatomical charts corresponding to test images are stored for each of a plurality of tests, such as blood tests. In addition, treatment methods and statistical data related to the efficacies of the treatment methods are stored correlated with each diagnostic result. In addition, the electronic medical texts include glossaries that explain the biological tissues of subjects and the names of diagnostic results in simple terms. Further, different comments are prepared for each range of values of test result values for tested items.

In the first embodiment, the comment information database 13 has stored therein three dimensional model images of a model subject, and three dimensional anatomical charts corresponding to the three dimensional model images, as images of healthy subjects. The three dimensional model images are three dimensional images obtained by imaging model subjects with medical imaging devices (X ray CT apparatuses, MRI apparatuses, etc., for example). These three dimensional images are constituted by a plurality of axial tomographic images. The comment information database 13 has stored therein three dimensional model images of model subjects for each sex and each age. In addition, three dimensional model images may be stored corresponding to other variables (for each height, for each weight, etc.).

The three dimensional anatomical charts are three dimensional anatomical charts corresponding to the stored three dimensional standard images, and are anatomical charts of the model subjects pictured in the three dimensional standard images. The three dimensional anatomical charts are constituted by anatomical charts corresponding to each of the axial tomographic images of the three dimensional standard images. The comment information database 13 stores a plurality of three dimensional standard images, and therefore stores a plurality of three dimensional anatomical charts corresponding thereto. The comment information database 13 also has stored therein data that indicates the names of each biological tissue region illustrated in the three dimensional anatomical charts.

Note that the comment information database 13 performs the functions of the template storing means 27 and the comment information storing means 28. Note that the present invention is not limited to the configuration of the present embodiment, and storage devices that constitute the template storing means 27 and the comment information storing means 28 may be configured as systems in various different formats in each of a plurality of hospitals.

The template storing means 27 has stored therein explanation templates having insertion regions, into which at least a portion of the diagnostic information and the comment information can be inserted. In the present embodiment, an explanation template is prepared for each of a plurality of disease names. A desired number of fields is provided in each explanation templates, and items to be inserted into each field are set in advance. Each field is provided with an insertion region, into which comments that explain symptoms unique to a patient, diseases, or symptoms, may be inserted. Not only words and sentences, but also photographs and anatomical charts may be inserted into the insertion regions. In addition, the template storing means 27 has stored therein a plurality of explanation templates having different levels of detail for each of a plurality of various diagnostic results.

The input means 21 is employed to input patient specifying information for a patient for whom a diagnostic result explanation report is to be generated, by detecting input via the input devices of the patient terminal 11, such as the mouse and the keyboard. Here, a registered user is prompted to input their user name and password. The input user ID, password, etc. are input to the user authenticating server 16, and the user authenticating server 16 is requested to perform user authentication. Then, the results of user authentication are received from the user authenticating server 16. In the case that the user ID and the password match, and it is confirmed that the user is a medical professional or a patient for whom access rights have been set for diagnostic result explanation reports, the user is prompted to input a patient ID corresponding to a diagnostic result explanation report which is desired to be viewed and to select a level of detail of explanation. The input patient ID is input to the diagnostic information obtaining means 22, and the input level of detail is input to the diagnostic result explanation report generating means 25.

The diagnostic information obtaining means 22 obtains diagnostic information regarding patients from the diagnostic information storing means 26, based on input patient specifying information. The input means 21 prompts users for whom access has been granted as a result of user authentication for input of patient ID's. The input patient ID's are input to the diagnostic information obtaining means 22. Then, the diagnostic information obtaining means 22 refers to the imaging observation report database 7 and the electronic chart database 9, to obtain patient information such as the sex, the age, the weight, and the height of the patient corresponding to the patient ID. In addition, the diagnostic information obtaining means 22 obtains diagnostic information, which includes diagnostic results which are described as medical opinions in electronic charts, for the patient corresponding to the patient ID. Note that in the present embodiment, the comment information obtaining means 24 obtains comment information from the comment information database 13 even in cases that a request to search diagnostic information is input via the diagnostic result explanation report generating means 25.

The template obtaining means 23 obtains explanation templates which are prepared for the diagnostic results obtained from the comment information database 13, based on the diagnostic results described in the obtained diagnostic information. In the present embodiment, the names of diseases are obtained as diagnostic results, and explanation templates corresponding to the obtained names of diseases are obtained. In addition, the diagnostic result explanation report generating apparatus of the present embodiment obtains explanation templates corresponding to input levels of detail of explanations. Note that the levels of detail are designated as three levels: a (simple); b (standard); and c (professional) in the present embodiment. The diagnostic result explanation report generating apparatus of the present invention is set such that explanation templates Ta having a level of detail a are obtained in the case that a level of detail is not specified. In addition, in the case that patients select level of detail b, templates Tb corresponding to the selected level are obtained.

The comment information obtaining means 24 obtains comment information from the comment information database 13. In the present embodiment, the comment information obtaining means 24 obtains comment information corresponding to explanation templates from the comment information database 13 in response to requests from the diagnostic result explanation report generating means 25.

The diagnostic result explanation report generating means 25 generates diagnostic result explanation reports by inserting necessary diagnostic information and comment information obtained from the diagnostic information storing means and the comment information storing means 28 into obtained templates. The diagnostic result explanation report generating means 25 stores the generated diagnostic result explanation reports in the diagnostic result explanation report managing server 15.

FIG. 3 is a diagram that illustrates an example of an explanation template. As illustrated in FIG. 3, the diagnostic result explanation report generating means 25 specifies search keywords correlated to information to be inserted into insertion regions of fields F1 through F7 of an obtained explanation template Ta. Then, the diagnostic result explanation report generating means 25 searches through the obtained diagnostic information and the obtained comment information using the search keywords correlated to information to be inserted. The results of the search are determined to be information to be inserted into the insertion regions of the explanation template. As necessary, the diagnostic result explanation report generating means 25 supplies the diagnostic information obtaining means 22 and the comment information obtaining means 24 with patient ID's and search keywords correlated to information to be inserted. In this case, the diagnostic information obtaining means 22 and the comment information obtaining means 24 search for information correlated to the search keywords, and obtain search results.

Note that the patient terminal has stored therein various glossaries. During the keyword search, the various search keywords are converted to synonymous keywords by known techniques, and searches are performed using the converted keywords as well. Thereby, correlated information can be detected even in cases that names of diseases and symptoms are described in abbreviated manners are in professional jargon in electronic charts and the like. The diagnostic information obtaining means 22 and the comment information obtaining means 24 obtain diagnostic information and comment information yielded by the search using the patient ID's and search keywords supplied by the diagnostic result explanation report generating means from the image information database 5, the image observation report database 7, the electronic chart database 9, and the comment information database 13.

Here, in the present embodiment, the diagnostic result explanation report generating means 25 has a function of determining information to be inserted into the insertion regions of explanation templates from among pieces of comment information corresponding to diagnostic information obtained for patients. Specifically, the diagnostic result explanation report generating means 25 determines explanatory text within a range that corresponds to test values for blood tests according to the results of blood tests of patients, and inserts the determined explanatory text. In addition, the diagnostic result explanation report generating means 25 determines explanatory text from among pieces of comment information that correspond to the names of diseases of patients, and inserts the determined explanatory text into the insertion regions.

The diagnostic result explanation report generating means 25 also has a function of determining anatomical charts and model images corresponding to obtained diagnostic images of patients, and inserting the determined anatomical charts and model images. The technique disclosed in Japanese Patent Application No. 2010-024587 is utilized as the method for determining the anatomical charts and model images corresponding to diagnostic images. Specifically, the diagnostic result explanation report generating means 25 specifies and obtains tomographic images (hereinafter, referred to as "medical tomographic images") of patients of which search keywords set for fields of explanation templates are correlated by physicians as additional data attached thereto, from among the three dimensional medical images of patients imaged by various modalities within the image information database 5, via the diagnostic information obtaining means 22. In the present embodiment, the three dimensional medical images are constituted by a plurality of axial tomographic images. Note that the three dimensional medical images obtained by the diagnostic information obtaining means 22 and the three dimensional model images stored in the comment information database 13 are those which are obtained by the same type of medical imaging apparatus (an X ray CT apparatus, for example).

The diagnostic result explanation report generating means 25 obtains three dimensional model images corresponding to patient specifying information (information such as sex and age) within obtained diagnostic information from the comment information database 13 via the comment information obtaining means 24. Then, the diagnostic result explanation report generating means 25 specifies tomographic images (hereinafter, referred to as "model tomographic images") corresponding to the specified medical tomographic images of patients, and determines the specified model tomographic images as images to be inserted into the insertion regions of templates.

Specifically, the diagnostic result explanation report generating means 25 administers a position aligning process, to specify model tomographic images that match the medical tomographic images at a predetermined match value or greater. In the present embodiment, the diagnostic result explanation report generating means 25 specifies standard tomographic images that most match medical tomographic images, from among the model tomographic images that match the medical tomographic images at the predetermined match value or greater. Note that model tomographic images that most match the medical tomographic images may be specified, regardless of whether the match value is greater than or equal to the predetermined match value. The technique disclosed in U.S. Patent Application Publication No. 20100231605 may be employed as the position aligning process.

The technique disclosed in U.S. Patent Application Publication No. 20100231605 will be described. First, standard coordinate positions of each slice image of a three dimensional standard image, and standard features of each of the slice images are recorded. Here, there are four features: a feature that indicates the roundness of the body of a subject as a whole, an air region feature that indicates the percentage of air regions in the subject; a bone region feature that indicates the percentage of bone regions in the subject; and a soft tissue feature that indicates the percentage of soft tissue in the subject. Then, the features of an obtained tomographic image are calculated, and the feature that most matches the calculated features is searched for. The coordinate position corresponding to the found feature is recorded as the coordinate position of the obtained tomographic image.

Further, the diagnostic result explanation report generating means 25 obtains three dimensional anatomical images (three dimensional anatomical charts) corresponding to the obtained three dimensional model images from the comment information database 13 via the comment information obtaining means 24. When the model tomographic images are specified, anatomical tomographic images that constitute the three dimensional anatomical charts corresponding to the model tomographic images are specified. That is, anatomical tomographic images that correspond to specified tomographic images that constitute the three dimensional medical images are specified from among the anatomical tomographic images that constitute the three dimensional anatomical charts obtained as comment information, and are determined as images to be inserted into the insertion regions of the templates.

The display control means 29 causes generated diagnostic result explanation reports to be displayed by the display of the patient terminal 11.

FIG. 4 is a flow chart that illustrates the processes for generating a diagnostic result explanation report according to the present embodiment. The processes by which the diagnostic result explanation report generating apparatus of the present embodiment generates a diagnostic result explanation report will be described in detail with reference to FIG. 4. A case in which a patient who has been diagnosed with liver cancer employs the patient terminal 11 to generate a diagnostic result explanation report will be described.

Blood tests, standard imaging of the chest, and imaging using an imaging agent of the chest are administered on the patient prior to the processes performed by the present embodiment. It is assumed that the obtained three dimensional medical images are stored in the image information database 5, image observation reports are generated by image diagnosis of the obtained images and stored in the image observation report database 7, and an electronic chart has been generated regarding the patient's answers to a questionnaire, blood test results, and comprehensive diagnostic results and stored in the electronic chart database 9.

Note that in the present embodiment, the user authenticating server 16 is configured to be accessible over the Internet. When the patient accesses a website administered by the hospital where he or she was examined, a screen that prompts the patient to input a user ID and a password is displayed. The patient terminal 11 receives input of the patient's user ID and password as patient specifying information, and inputs them to the user authenticating server 16 (S01).

The patient terminal 11 receives the results of authentication from the user authenticating server 16. If the user ID and the password match, and it is confirmed that access is being attempted by a medical professional or a patient for whom access rights with respect to diagnostic result explanation reports have been set, a work screen is displayed (S02: OK).

The patient terminal 11 prompts the user to input a patient ID regarding whom a diagnostic result explanation report is to be viewed and to select a level of detail. An input patient ID is input to the diagnostic information obtaining means 22, and an input level of detail is input to the diagnostic result explanation report generating means 25. Next, the diagnostic information obtaining means 22 obtains diagnostic information regarding a patient from each of the databases that have diagnostic information stored therein, based on the input patient ID (S03). In the case being described here, a disease name "liver cell carcinoma" is obtained as a diagnostic result.

The template obtaining means 23 obtains an explanation template Ta corresponding to "liver cell cancer", based on the diagnostic result (liver cell cancer) and the level of detail input at step S03, and stores the template Ta in a memory (S04).

As illustrated in FIG. 3, the explanation template Ta has: a basic patient information field F1, in which basic information regarding a patient, such as the name, the sex, the date of birth, the height, the weight, and blood type of the patient are to be inserted; a blood test field F2; a test explanation field F3 for explaining the results of blood tests; an image diagnosis result field F4 for inserting tomographic images obtained by a CT apparatus; an image diagnosis result explanation field F5 for explaining the results of image diagnosis; a diagnostic result field F6; and a diagnostic result explanation field F7 for explaining diagnostic results. One or more insertion regions K11, etc. are provided in each field. In addition, keywords K11, etc. for searching are correlated with each of the insertion fields K11, etc.

The diagnostic information obtaining means 22 and the comment information obtaining means 24 obtain information necessary for the obtained explanation template (S05).

First, the diagnostic information obtaining means 22 obtains information regarding the patient from the databases, based on the patient ID. In the present embodiment, the patient's electronic chart is obtained from the diagnostic information in order to obtain at least the patient's diagnostic result in step S03. All other pieces of diagnostic information related to the patient are also obtained at this step. Note that all pieces of diagnostic information related to the patient may be obtained at once in step S03, or different pieces of diagnostic information may be obtained at various timings during each process step as necessary. In addition, the contents to be obtained may be only those necessary for the template, or all contents may be obtained.

Next, the comment information obtaining means 24 obtains comment information. Pieces of information to be searched for are set and correlated for each field of each template.

In the explanation template Ta of the present example, the insertion regions into which pieces of comment information are to be inserted are provided in the blood test explanation field F3, the image diagnosis result explanation field F5, the diagnostic result explanation field F7. The comment information obtaining means 24 obtains blood test explanation information to be inserted into the blood test explanation field F3 using the type of blood test as a keyword. The comment information obtaining means 24 obtains comment information to be inserted into the diagnostic result explanation field F7 using the name of the disease, which is a confirmed diagnosis of the patient, as a keyword. Here, if the name of the disease is the proper name for liver cell cancer, the comment information obtaining means 24 searches through the comment information using the proper name for liver cell cancer as a keyword for pieces of information to be inserted into the insertion region K71 of the diagnostic result explanation field F7.

Next, the diagnostic result explanation report generating means 25 searches among the pieces of obtained diagnostic information and the pieces of obtained comment information for information to be inserted into the insertion regions of the fields F1 through F7 using the keywords k11, etc., which are correlated with each insertion region. The diagnostic result explanation report generating means 25 then determines the hits yielded by the search as pieces of information to be inserted into the insertion regions (S06).

At this step, first, the diagnostic result explanation report generating means 25 performs keyword searches by each of the keywords k11, etc., correlated with diagnostic information related to the fields F1, F2, F4, and F6 from among the pieces of obtained information. Then, the diagnostic result explanation report generating means 25 determines the hits yielded by the searches as pieces of information to be inserted into the insertion regions.

Specifically, the diagnostic result explanation report generating means 25 searches for and determines text and numbers that correspond to keyword k11 "patient name", keyword k12 "sex", keyword k13 "date of birth", keyword k14 "height", keyword k15 "weight", and keyword k16 "blood type" from among the obtained pieces of information as pieces of information to be inserted into the insertion regions K11 through K16 within the basic patient information field F1.

The diagnostic result explanation report generating means 25 searches for and determines a GTP value, a value for Item 2 and text that correspond to keywords k21 "GTP value" and keyword k22 "Item 2" from among the obtained pieces of information as pieces of information to be inserted into the insertion regions K21 and K22 within the blood test field F2.

The diagnostic result explanation report generating means 25 searches for and determines the contents of a first medical opinion and the contents of a second medical opinion that correspond to keyword k41 "radiology department and medical opinion 1", keyword k42 "representative standard tomographic image of the disease", keyword k43 "representative tomographic image obtained using imaging agent of the disease", and keyword k44 "radiology department and medical opinion 2" from among the obtained CT diagnostic images and the obtained image observation reports as pieces of information to be inserted into the insertion regions K41 and K44 within the image diagnosis result field F4. Note that among the diagnostic images, representative tomographic images of the disease are specifiable by identifiable keywords being added to tag data or the like. Here, a standard tomographic image 141 which is obtained by CT imaging without injecting an imaging agent and a tomographic image 142 obtained by imaging using an imaging agent are determined as pieces of information to be inserted into insertion regions K42 and K43 within the image diagnosis result field F4.

In addition, the diagnostic result explanation report generating means 25 searches the obtained electronic chart of the patient regarding keyword k61 "name of disease" for an insertion region K61, and determines a name of a disease corresponding to the confirmed diagnosis as a piece of information to be inserted into the insertion region K61 of the diagnostic result field F6. Note that in the case that an abbreviated name or the like is described as the name of a disease, the description in the electronic chart may be converted to the official name of the disease and determined as a piece of information to be inserted into the insertion region K61 of the diagnostic result field F6.

Next, the diagnostic result explanation report generating means 25 searches pieces of information to be inserted from among the obtained comment information, and determined the search results to be pieces of information to be inserted into insertion regions.

In the present embodiment, portions of the keywords correlated with the insertion regions within the explanation fields F3, F5, and F7 are set based on pieces of information determined to be inserted into the insertion regions of the diagnostic information fields F1, F2, F4, and F6. That is, the diagnostic result explanation report generating means 25 determines pieces of comment information to be inserted into the examination explanation field F3, based on the diagnostic information determined in step S05.

First, the blood test explanation field F3 will be described. Note that pieces of blood test explaining information obtained by the comment information obtaining means 24 has normal and abnormal ranges of GTP values for each age. Terms and text to be inserted in the case that a GTP value within a normal range is obtained and terms and text to be inserted in the case that a GTP value within an abnormal range obtained are both prepared. In addition, normal ranges, abnormal ranges, diagnostic standards of test results, and suspected diseases associated with test results in abnormal ranges are stored in the comment information database for each test.

The diagnostic result explanation report generating means 25 judges whether the patient's GTP value is within a normal range or an abnormal range for the patient's age, from the obtained blood test explanation information. Next, the diagnostic result explanation report generating means 25 detects terms or text to be inserted in the case that the patient's GTP value is within a normal range or terms or text to be inserted in the case that the patient's GTP value is within an abnormal range from the blood test explanation information, according to the results of judgment. Then, the diagnostic result explanation report generating means 25 determines pieces of information corresponding to keywords k31 through k35 as pieces of information to be inserted into insertion regions K31 through K35 within the test explanation field F3, based on the detected information.

Note that the search keywords for searching through the diagnostic information and the comment information may be determined by a variety of desired methods. A single keyword may be set for each field related to test results and the like, or a keyword may be set for each insertion region within the fields. In addition, a plurality of keywords may be set for a single insertion region.

Next, the diagnostic result explanation report generating means 25 specifies a model tomographic image 152 that corresponds to the standard tomographic image 141 based on the three dimensional model image and the three dimensional anatomical chart obtained by the comment information obtaining means 24, using the method described above. Thereafter, an anatomical chart 151 corresponding to the specified model tomographic image 152 is specified, and the two specified images are determined to be pieces of information to be inserted into insertion regions K53 and K52 of the image diagnosis result explanation field F5. In addition, information correlated to the anatomical portion correlated to the anatomical chart 151 is also displayed in the insertion region K52.

The diagnostic result explanation report generating means 25 analyzes the text or terms to be described for each of the medical opinion 1 and the medical opinion 2. Professional jargon and abbreviations are extracted from the analyzed text and terms, the comment information obtaining means 24 is caused to perform keyword searches in the comment information database 13. The professional jargon may be converted to alternate expressions or explanatory text may be added, as necessary. The pieces of information obtained as a result are determined as pieces of information to be inserted into the insertion regions K51 and K53 of the image diagnosis result explanation field F5.

Here, the image observation report comment information related to liver cell cancer from among the obtained pieces of comment data describe the characteristics of disease symptoms that appear in standard tomographic images and methods for discriminating healthy states and abnormal states for each modality and each imaging method employed to obtain the tomographic images. If information that corresponds to the imaging conditions of the standard tomographic image 141 of the patient in the image observation report comment information related to liver cell cancer, the diagnostic result explanation report generating means 25 determines such information as information to be inserted into the insertion regions K51 and K54 of the image diagnosis result explanation field F5.

The diagnostic result explanation report generating means 25 also determines pieces of information to be inserted into the diagnostic result explanation field F7 based on the obtained comment information. Explanations related to the characteristics of diseases, such as common names of diseases, symptoms of liver cell cancer, standard treatments, statistical data regarding efficacies of treatment methods, etc., are extracted by keyword searches, and determined to be pieces of information to be inserted into an insertion region K71 of the diagnostic result explanation field F7.

Note that the searches for the comment information at step S05 may be performed prior to or simultaneously with the search for the diagnostic information. As an alternative, the searches may be performed as necessary when pieces of information among the comment information to be inserted into the insertion regions are determined at step S06. As a further alternative, each of the databases may be directly searched in for pieces of diagnostic information or pieces of comment information to be inserted into the insertion regions.

The diagnostic result explanation report generating means 25 determines necessary pieces of diagnostic information and comment information from among the information obtained from the diagnostic information storing means 26 and the comment information storing means 28 as described above. The pieces of information determined to be necessary are inserted into the explanation template Ta to generate a diagnostic result explanation report Ra. Then, the diagnostic result explanation report generating means 25 stores the generated diagnostic result explanation report in the diagnostic result explanation report managing server 15 (S07).

Note that the diagnostic information obtaining means 22 may obtain all of the diagnostic information related to the patient from the diagnostic information storing means 26 at step S03. Alternatively, only a portion of the diagnostic information related to the patient may be obtained at step S03, and other diagnostic information may be obtained from the diagnostic information storing means 26 as necessary at step S05.

Figure 5:
FIG. 5 is a diagram that illustrates an example of a generated diagnostic result explanation report.

The display control means 29 obtains the diagnostic result explanation report Ra generated by the diagnostic result explanation report generating means 25, and displays the diagnostic result explanation report Ra, such as that illustrated in FIG. 5, on the display of the patient terminal 11 (S08).

According to the first embodiment, the patient specifying information that specifies patients are stored, the diagnostic information that includes diagnostic results related to patients are stored, and the explanation templates having insertion regions, into which at least a portion of the diagnostic information and the comment information can be inserted, are stored for each of the various diagnostic results. Patient specifying information of a patient regarding whom a diagnostic result explanation report is to be generated is input, and diagnostic information for a patient is obtained from among the stored diagnostic information, based on the input patient specifying information. Next, an explanation template, which is prepared for a diagnostic result is obtained, based on a diagnostic result included in the obtained diagnostic information. Finally, the diagnostic result explanation report is generated by inserting necessary diagnostic information and comment information from among the obtained diagnostic information and stored comment information into the obtained explanation template. Therefore, diagnostic result explanation reports, in which diagnostic information of patients and comment information related to the diagnostic information of patients are inserted, can be generated. As a result, user comprehension of diagnostic results can be improved.

In the present embodiment, the template storing means 27 stores a plurality of explanation templates having different levels of detail for each of the various diagnostic results. In this case, diagnosis result explanation reports having different levels of detail can be generated. Therefore, diagnosis result explanation reports corresponding to user comprehension levels can be generated, and as a result, the comprehension of diagnostic results can be improved.

In addition, the input means 21 inputs the level of detail of explanations, and the template obtaining means 23 obtains an explanation template corresponding to the input level of detail. In this case, diagnosis result explanation reports having levels of detail corresponding to the input level of detail can be generated, and the comprehension of diagnostic results can be improved.

A pull down menu for switching the level of detail of the diagnostic result explanation report may be displayed by clicking the right mouse button, user operations may be detected, and a diagnostic result explanation report that employs an explanation template having a newly selected level of detail may be displayed, for example.

When a command to generate a diagnostic result explanation report is received, a diagnostic result explanation report may be generated using only one of the explanation templates Ta, Tb, and Tc corresponding to a specified level of detail. Alternatively, diagnostic result explanation reports may be generated using the explanation templates Ta, Tb, and Tc corresponding to all levels of detail.

In the present embodiment, the diagnostic result explanation report generating means 25 determines pieces of comment information to be inserted into the insertion regions for explanations based on the diagnostic information. Therefore, appropriately customized diagnostic result explanation reports can be flexibly generated for diagnostic results of patients, and the comprehension of diagnostic results can be improved.

The diagnostic result explanation report generating means 25 inserts a diagnostic image from among the diagnostic information of the patient into an insertion region of the template. Therefore, diagnosis result explanation reports that include diagnostic images of patients can be generated, and the comprehension of diagnostic results can be improved.

Further, the diagnostic result explanation report generating means 25 inserts an anatomical chart corresponding to the diagnostic image of the patient from among the diagnostic information into an insertion region of the template. Therefore, the diagnostic image can be better understood by referring to the anatomical chart in the completed diagnostic result explanation report, thereby improving the comprehension of diagnostic results. Similarly, the diagnostic result explanation report generating means 25 inserts a model image that represents the same portion as that represented by the diagnostic image of the patient from among the diagnostic information into an insertion region of the template. Therefore, the diagnostic image can be better understood by referring to the model image in the completed diagnostic result explanation report, thereby improving the comprehension of diagnostic results.

The present embodiment is equipped with the diagnostic result explanation report storing means 15 for storing the diagnostic result explanation reports generated by the diagnostic result explanation report generating means 25. Therefore, the diagnostic result explanation reports can be stored or referred to as necessary. As a result, the diagnostic result explanation reports can be actively utilized.

Figure 6:
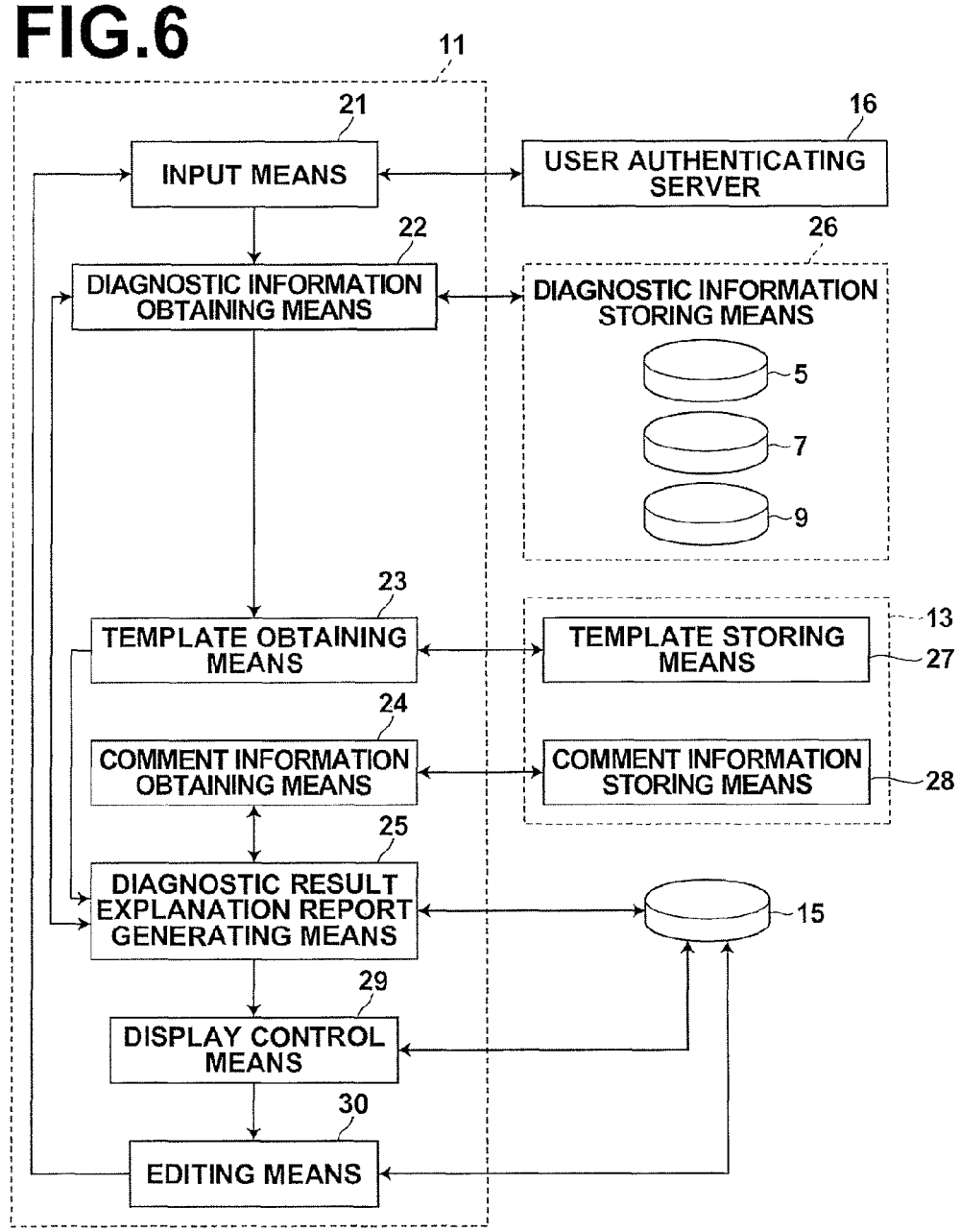
FIG. 6 is a functional block diagram of a diagnostic result explanation report generating apparatus according to a modification to the first embodiment of the present invention.

FIG. 6 is a functional block diagram of a diagnostic result explanation report generating apparatus according to a modification to the embodiment of the present invention. As illustrated in FIG. 6, an editing means 30 for editing stored diagnostic result explanation reports may be further provided to the diagnostic result explanation report generating apparatus of the first embodiment. The editing means 30 obtains information related to additions and changes to text input by a user via the input means 21. Then, generated diagnostic result explanation reports or diagnostic result explanation reports obtained from the diagnostic result explanation report database 15 are updated in a memory to reflect the obtained information. In this case, the diagnostic result explanation reports can be edited as necessary, and the generated or edited diagnostic result explanation reports can be stored. Therefore, the generated or edited diagnostic result explanation reports can be actively utilized.

In the first embodiment, a patient's computer, which is connected to the network 19 via the Internet and in which necessary portions of the diagnostic result explanation report generating program of the present invention are installed, functions as the patient terminal 11. That is, the input means 21 of the diagnostic result explanation report generating apparatus inputs patient specifying information via the Internet. For this reason, patients have more choices with respect to locations and times at which diagnostic result explanation reports are generated by the diagnostic result explanation report generating apparatus, and may do so at their homes instead of going to hospitals. Thereby, the burden placed on patients is greatly reduced.

Note that it is preferable for necessary portions of the diagnostic result explanation report generating program of the present invention to be installed in each of the work stations 3 and 10 or patient terminals (not shown) provided at hospital reception areas and waiting rooms and connected to the network 19 via wired or wireless LAN's, to enable diagnostic result explanation reports to be generated. In this case, patients and receptionists can easily generate and refer to diagnostic result explanation reports as necessary. Such diagnostic result explanation reports can be actively utilized to explain diagnostic results, by being shown to patients during explanations of their diagnostic results at medical facilities, for example. By adopting this configuration, more effective and active utilization of diagnostic result explanation reports can be facilitated.

Medical facilities may generate diagnostic result explanation reports and store them in the diagnostic result explanation report database 15. In this case, departments of hospitals and patients can refer to diagnostic result explanation reports of desired patients, and active utilization of information is facilitated.

The present embodiment performs keyword searches using synonyms and alternate expressions. Therefore, more information can be appropriately obtained. Note that various known methods may be employed to set the search keywords.

It is preferable for the contents of the explanation templates to be freely designable according to departments of hospitals and intended uses. Explanation templates that compile diagnostic results by a plurality of different departments of hospitals for each disease name may be prepared. In this case, diagnostic result explanation reports that compile diagnostic information of a plurality of departments of hospitals can be generated, the need for patients to solicit physicians in each department for explanations of diagnostic results can be obviated, and comprehensive understanding can be assisted. In addition, diagnostic information generated to judge various test results may be accompanied with explanations regarding the bases and histories of diagnoses. Thereby, patient comprehension can be greatly improved compared to the current state, in which patients find it difficult to judge examination results due to their lack of professional knowledge.

In addition, understanding of the contents of diagnosis is greatly improved, by inserting information that physicians employ as judgment criteria, such as information regarding healthy states and information regarding abnormal states, in the explanation templates as in the present embodiment.

Understanding of diagnostic images requires a high level of medical knowledge, due to advances and specialization of image diagnostic techniques. According to the present embodiment, the diagnostic result explanation reports Ra are provided with easily understandable explanations related to portions corresponding to patients' diagnostic images and names of diseases. Therefore, patient comprehension can be greatly improved. In addition, understanding of specialized professional content by patients is also assisted, by adding judgment criteria employed during image observation to the diagnostic result explanation reports Ra.

In addition, it is preferable for the comment information to be employed in the embodiments to further include lifestyle habit information. Note that the lifestyle habit information includes pieces of information that represent indices of favorable lifestyle habits (or unfavorable lifestyle habits). Such pieces of information include information related to amount of alcohol intake, the amount of tobacco intake, the contents of diet, the amount of food intake, the type and amount of exercise, amount of sleep, etc.

The following example may be considered. First, lifestyle habit information, in which favorable lifestyle habits are correlated to each disease name, is generated and stored as a piece of comment information in the comment information database 13. Explanation templates having lifestyle habit fields, into which lifestyle habit information can be inserted, are stored in the template storing means 27. In the case that obtained explanation templates have lifestyle habit fields, the diagnostic result explanation report generating means 25 obtains lifestyle habit information correlated to the disease name of the patient for whom the diagnostic result explanation report is being generated. The obtained lifestyle habit information is inserted into the lifestyle habit fields, and the diagnostic result explanation report is generated. Note that the lifestyle habit information may be generated and inserted using other diagnostic results other instead of the disease name.

In this case, the need of patients to obtain points of lifestyle habits to be improved can be satisfied, in addition to enabling understanding information regarding examinations and treatments administered at hospitals.

Figure 7:
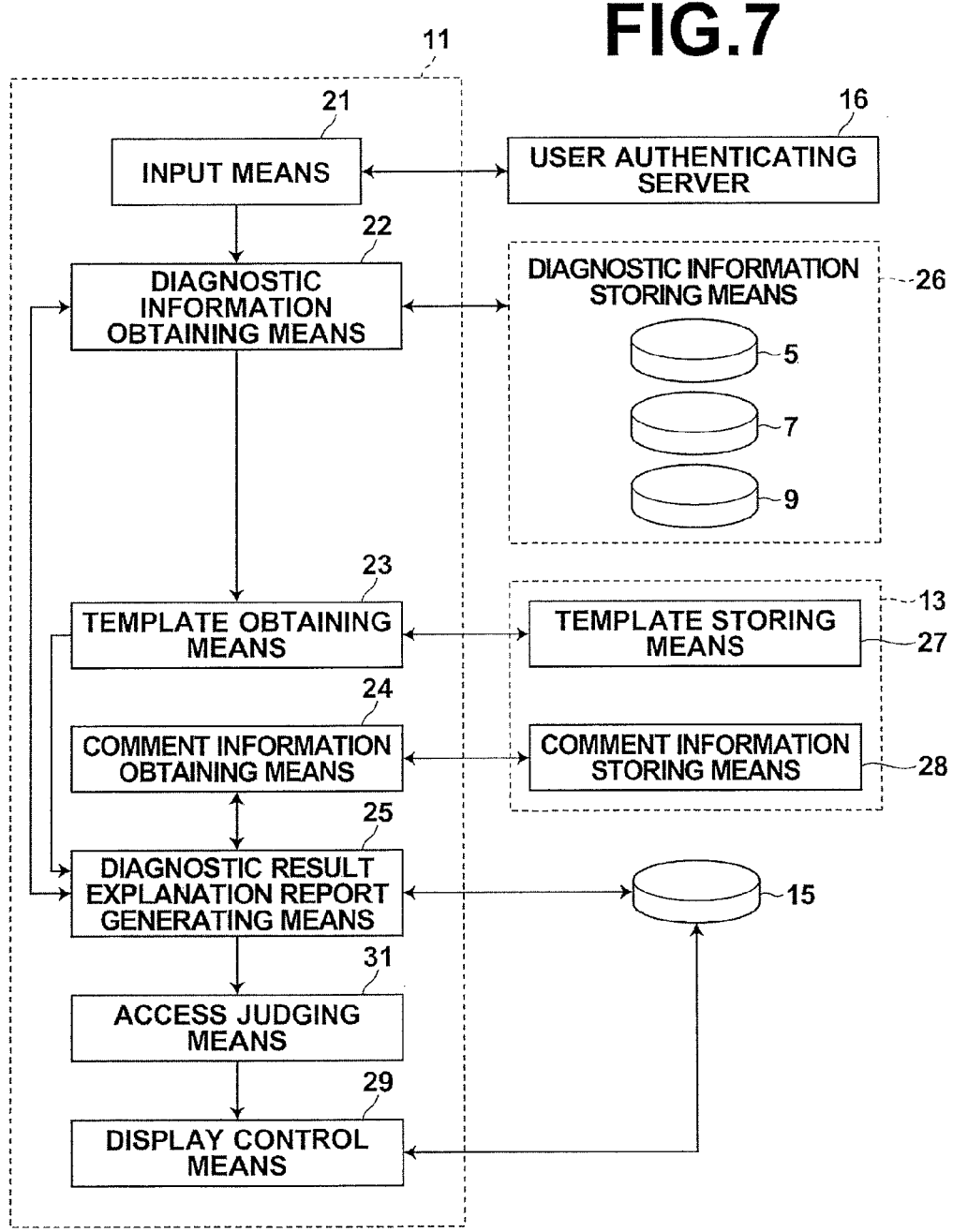
FIG. 7 is a functional block diagram of the diagnostic result explanation report generating apparatus according to a second embodiment of the present invention.

Hereinafter, a second embodiment of the present invention will be described with reference to FIG. 7. FIG. 7 is a functional block diagram of the diagnostic result explanation report generating apparatus according to the second embodiment. The second embodiment is basically of the same configuration as the diagnostic result explanation report generating apparatus of the first embodiment, but is further equipped with an access judging means 31, for soliciting a third party, such as a physician that manages the diagnostic result explanation reports, for confirmation regarding the contents of the diagnostic result explanation reports, and judges whether the diagnostic result explanation reports are to be accessible to users such as patients after receiving the confirmation results. The points that differ from the first embodiment will be described in the following embodiments, and detailed descriptions will be omitted with respect to points which are the same as those of the first embodiment.

After a diagnostic result explanation report is generated by processes which are the same as those of S01 through S07 of the first embodiment, the access judging means 31 specifies contact information for a hospital staff member such as the attending physician of the patient for whom the diagnostic result explanation report was generated from the diagnostic information. An e-mail or the like is sent to the hospital staff member to confirm the contents of the diagnostic result explanation report.

The diagnostic medical work station 10 which is utilized by attending physicians or other hospital staff display generated diagnostic result explanation reports using arbitrary editing applications based on operations of input devices input by the attending physicians or hospital staff members. In the case that the hospital staff member edits the diagnostic result explanation report as necessary, the edited diagnostic result explanation report is stored in the diagnostic result explanation report database 15 based on operations of input devices input by the attending physician or another hospital staff member.

In the case that access to the diagnostic result explanation report is permitted, the diagnostic medical work station 10 notifies the access judging means 31 that access is to be granted. Then, the access judging means 31 transmits a command to the display control means 29 to load the diagnostic result explanation report from the diagnostic result explanation report database 15 to a patient terminal 11 and to display the diagnostic result explanation report on the display screen of the patient terminal 11. On the other hand, in the case that access to the diagnostic result explanation report is denied, the diagnostic medical work station 10 notifies the access judging means 31 that access is to be denied via e-mail or the like. Then, the access judging means 31 transmits a command to the display control means 29 to display a message that the diagnostic result explanation report cannot be displayed on the screen of a patient terminal.

By providing the access judging means 31 as described above, the contents of diagnostic result explanation reports can be prevented from being provided to patients unintentionally, according to the contents of the diagnostic result explanation report. In addition, in the case that the hospital staff members such as physicians are enabled to edit the contents of the diagnostic result explanation reports, the hospital staff members can appropriately manage the contents of the diagnostic result explanation reports, and diagnostic result explanation reports having more accurate contents can be provided to patients.

A third embodiment will be described hereinafter. The third embodiment differs from the first embodiment in that the diagnostic result explanation report generating means 25 of the diagnostic result explanation report generating apparatus is equipped with a similar report extracting means 32 that extracts a diagnostic result explanation report having diagnostic information similar to diagnostic information of a patient for whom a diagnostic result explanation report is to be generated as a similar report, from among past diagnostic result explanation reports stored in the diagnostic result explanation report database 15.

The similar report extracting means 32 obtains previously generated diagnostic result explanation reports which are stored in the diagnostic result explanation report database 15 as comparative diagnostic result explanation reports (comparative reports). The similar report extracting means 32 extracts a diagnostic result explanation report that has disease names that match the disease name of a patient for whom a diagnostic result explanation report is to be generated, and that has diagnostic information similar to diagnostic information of the patient for whom the diagnostic result explanation report is to be generated, as a similar diagnostic result explanation report (similar report).

The similar report extracting means 32 may employ various techniques to judge the similarity between the diagnostic information of the patient for whom the diagnostic result explanation report is to be generated and the diagnostic information of the comparative reports. In addition, the items of diagnostic information which are employed to judge the similarity between diagnostic information may be selected arbitrarily.

For example, it may be judged that the diagnostic information are similar in the case that: (a) numerical values that represent test results are close to each other, based on the numerical values that represent test results included in the diagnostic information. The numerical values that represent test results may be judged to be close to each other in cases that the numerical values fall into the same numerical range from among numerical ranges that the numerical values that represent test results are divided into based on medical standards.

Alternatively, it may be judged that the diagnostic information are similar in the case that: (b) the features of tomographic images included in diagnostic data and the medical opinions regarding diagnostic images are similar; (c) the histories of test results for the same tests administered a plurality of times are similar; or (d) basic information regarding patients, such as the sex, age, and weight, or symptoms such as coughing and fever and the degrees thereof are the same or similar.

Here, a case will be described in which a similar report is extracted using the technique disclosed in Japanese Unexamined Patent Publication No. 2007-286945 as an example that satisfies the evaluation criteria of case (b). Note that the technique disclosed in Japanese Unexamined Patent Publication No. 2003-122845 or the technique disclosed in Japanese Unexamined Patent Publication No. 2004-288047 may be employed to judge similarity among diagnostic information based on the evaluation criteria of cases (a), (c), or (d).

After processes which are the same as those of S01 through S05 of the first embodiment are executed, the similar report extracting means 32 extracts the disease name and a first set of diagnostic images of the same subject obtained by different imaging modalities from diagnostic information obtained by the diagnostic information obtaining means 22. Next, the similar report extracting means 32 obtains past diagnostic result explanation reports stored in the diagnostic result explanation report database 15 as comparative reports. In the case that the disease name of a comparative report matches the obtained disease name, a plurality of diagnostic images (a plurality of comparative diagnostic images) correlated to the comparative report having an imaged portion and imaging modalities in common as the first set of diagnostic images. Next, the similar report extracting means 32 calculates the degrees of similarity among the diagnostic images of the patient for whom a diagnostic result explanation report is to be generated and the comparative diagnostic images, using the technique disclosed in Japanese Unexamined Patent Publication No. 2007-286945. The similar report extracting means 32 repeats the calculation of the degrees of similarity with respect to all of the past diagnostic result explanation reports having the same disease name stored in the diagnostic result explanation report database 15, and obtains a comparative report correlated with the comparative diagnostic images having the highest degrees of similarity as the similar report. Note that the comparative diagnostic images may be images which are inserted in the comparative reports themselves, or diagnostic images which are included in diagnostic information correlated to the comparative reports.

Then, the diagnostic result explanation report generating means 25 obtains the contents of predetermined insertion items from among the items to be inserted into an explanation template, such as treatments, from the similar report, and inserts the obtained contents into the explanation template. In addition, the diagnostic result explanation report generating means 25 inserts pieces of diagnostic information and comment information into insertion regions other than the above predetermined insertion, to generate the diagnostic result explanation report, which is then stored in the database 15. The display control means 29 performs a process which is the same as that of S08 of the first embodiment, to display the diagnostic result explanation report on the display screen.

The third embodiment enables the contents of the similar report to be employed to generate a diagnostic result explanation report for the patient for whom the diagnostic result explanation report is to be generated. For this reason, specific diagnostic information, such as the results and courses of treatments for another patient who has been diagnosed with the same disease and who has similar patient information, such as age and weight, or similar symptoms, can be inserted in the generated diagnostic result explanation report. Accordingly, information effective to further improve the patient's understanding can be provided. In addition, effective information that the patient can refer to may be provided, by inserting lifestyle habit information of a patient who has similar patient information, such as age and weight.

The diagnostic result explanation reports which are generated by the embodiments described above may be shown to physicians at hospitals other than those at which the diagnostic result explanation reports were generated, as diagnosis references. For example, patients with a plurality of diseases who are being treated at different hospitals for each disease may employ their diagnostic result explanation reports to explain their disease histories and the like.

The embodiments have been described as cases in which the functions of the diagnostic result explanation report generating apparatuses were realized by installing the diagnostic result explanation report generating program of the present invention into a plurality of apparatuses that constitute a system at a medical facility. However, as would be clear to those skilled in the art, it is possible to install the diagnostic result explanation report generating program into systems of various configuration to realize the functions of the diagnostic result explanation report generating apparatus.

What is claimed is:

1. A diagnostic result explanation report generating apparatus, comprising:
    a diagnostic information storing section for storing diagnostic information, which includes patient specifying information that specifies a patient and diagnostic results for the patient, wherein the diagnostic results include a diagnosed disease of the patient and test results of the patient;
    a comment information storing section for storing comment information regarding various diagnostic results;
    a template storing section for storing explanation templates having insertion regions, wherein the explanation templates are prepared for each of the various diseases respectively, and the insertion regions are configured such that at least a portion of the diagnostic information and the comment information is inserted thereto according to each disease;
    an input section, for inputting patient specifying information of a patient regarding whom a diagnostic result explanation report is to be generated;
    a diagnostic information obtaining section, for obtaining diagnostic information for a patient from the diagnostic information storing section, based on the input patient specifying information;
    a template obtaining section, for obtaining an explanation template which is included in the obtained diagnostic information;
    a comment information obtaining section, for obtaining comment information corresponding to the insertion regions of the obtained explanation template from the comment information storing section; and
    a diagnostic result explanation report generating section, for determining necessary diagnostic information and comment information obtained from the diagnostic information storing section and the comment information storing section to be information to be inserted into the insertion regions and inserting the determined information to be inserted into the insertion regions of the obtained explanation template, to generate a diagnostic result explanation report.

2. A diagnostic result explanation report generating apparatus as defined in claim 1, wherein:
    the template storing section stores a plurality of explanation templates having different levels of detail for each of the various diagnostic results.

3. A diagnostic result explanation report generating apparatus as defined in claim 2, wherein:
    the input section also inputs the level of detail of explanations; and
    the template obtaining section obtains an explanation template corresponding to the input level of detail.

4. A diagnostic result explanation report generating apparatus as defined in claim 1, wherein:
    the diagnostic result explanation report generating section inserts a diagnostic image from among the diagnostic information of the patient into an insertion region of the template.

5. A diagnostic result explanation report generating apparatus as defined in claim 4, wherein:
    the diagnostic result explanation report generating section inserts an anatomical chart corresponding to the diagnostic image of the patient from among the diagnostic information into an insertion region of the template.

6. A diagnostic result explanation report generating apparatus as defined in claim 4, wherein:
    the diagnostic result explanation report generating section inserts a model image that represents the same portion as that represented by the diagnostic image of the patient from among the diagnostic information into an insertion region of the template.

7. A diagnostic result explanation report generating apparatus as defined in claim 1, wherein:
    the input section inputs the patient specifying information via the Internet.

8. A diagnostic result explanation report generating apparatus as defined in claim 1, further comprising:
    a diagnostic result explanation storing section, for storing the diagnostic result explanation reports generated by the diagnostic result explanation report generating section; and
    an editing section, for editing the stored diagnostic result explanation reports.

9. A diagnostic result explanation report generating apparatus as defined in claim 1, wherein:
    the diagnostic result explanation report generating section specifies at least one of search keywords correlated to information to be inserted into the insertion regions of the obtained explanation template, the comment information obtaining section searches information corresponding to the search keywords through the obtained diagnostic information and/or the obtained comment information, the diagnostic result explanation report generating section determines the searched information corresponding to the search keywords to be the information to be inserted into the insertion regions of the explanation template.

10. A diagnostic result explanation report generating apparatus as defined in claim 9, wherein:

the diagnostic result explanation report generating section specifies at least one of addition search keywords according to the diagnostic result of the patient which is determined to be the information to be inserted into the insertion regions of the explanation template, the comment information obtaining section searches information corresponding to the additional search keywords through the obtained comment information, the diagnostic result explanation report generating section determines the searched information corresponding to the additional search keywords to be the information to be inserted into the insertion regions of the explanation template.

11. A diagnostic result explanation report generating method using a computer, comprising:

storing diagnostic information, which includes patient specifying information that specifies a patient and diagnostic results for the patient, wherein the diagnostic results include a diagnosed disease of the patient and test results of the patient;

storing comment information regarding various diagnostic results;

storing explanation templates having insertion regions, wherein the explanation templates are prepared for each of the various diseases respectively, and the insertion regions are configured such that at least a portion of the diagnostice information and the comment information is inserted thereto according to each disease:

inputting patient specifying information of a patient regarding whom a diagnostic result explanation report is to be generated;

obtaining diagnostic information for a patient from among the stored diagnostic information, based on the input patient specifying information;

obtaining an explanation template corresponding to the diagnosed disease of the patient which is included in the obtained diagnostic information;

obtaining comment information corresponding to the insertion regions of the obtained explanation template from among the stored comment information; and determining using the computer, necessary diagnostic information and comment information from among the obtained diagnostic information and stored comment information to be information be inserted into the insertion regions and inserting the determined information to be inserted into the insertion regions of the obtained explanation template, to generate a diagnostic result explanation report.

12. A non-transitory readable recording medium having a program recorded therein, the program causing a computer to function as:

a diagnostic information storing section for storing diagnostic information, which includes patient specifying information that specifies a patient and diagnostic results for the patient, wherein the diagnostic results include a diagnose disease of the patient and test results of the patient;

a comment information storing section for storing comment information regarding various diagnostic results;

a template storing section for storing explanation templates having insertion regions, wherein the explanation templates are prepared for each of the various diseases respectively, and the insertion regions are configured such that at least a portion of the diagnostic info ion and the comment information is inserted thereto according to each disease;

an input section, for inputting patient specifying information of a patient regarding whom a diagnostic result explanation report is to be generated;

a diagnostic information obtaining section, for obtaining diagnostic information for a patient from the diagnostic information storing section, based on the input patient specifying information;

a template obtaining section, for obtaining an explanation template corresponding to the diagnosed disease of the patient which is included in the obtained diagnostic information;

a comment information obtaining section, for obtaining comment information corresponding to the insertion regions of the obtained explanation template from the comment information storing section; and a diagnostic result explanation report generating section, for determining necessary diagnostic information and comment information obtained from the diagnostic information storing section and the comment information storing section to be information to be inserted into the insertion regions and inserting the determined information to be inserted into the insertion regions of the obtained explanation template, to generate a diagnostic result explanation report.

* * * * *